US012721962B2

(12) United States Patent
Strauss et al.

(10) Patent No.: US 12,721,962 B2
(45) Date of Patent: Sep. 1, 2026

(54) DIFFUSER DEVICE

(71) Applicants: John Laurence Strauss, Mies (CH); Stephan Laurence Strauss, Ecublens (CH); Larry Nouvel, Plano, TX (US)

(72) Inventors: John Laurence Strauss, Mies (CH); Stephan Laurence Strauss, Ecublens (CH); Larry Nouvel, Plano, TX (US)

( * ) Notice: Subject to any disclaimer, the term of this patent is extended or adjusted under 35 U.S.C. 154(b) by 473 days.

(21) Appl. No.: 18/105,652

(22) Filed: Feb. 3, 2023

(65) Prior Publication Data

US 2024/0261529 A1 Aug. 8, 2024

(51) Int. Cl.

*A61M 16/14* (2006.01)
*A01K 15/00* (2006.01)
*A61D 7/00* (2006.01)
*A61K 9/00* (2006.01)
*A61L 9/12* (2006.01)
*C09K 3/30* (2006.01)

(52) U.S. Cl.

CPC ............. *A61M 16/14* (2013.01); *A01K 15/00* (2013.01); *A61K 9/0043* (2013.01); *C09K 3/30* (2013.01)

(58) Field of Classification Search

CPC ..... A61M 16/14; A01K 15/00; A61K 9/0043; A61K 9/007; A61L 9/12; A61D 7/00
See application file for complete search history.

(56) References Cited

U.S. PATENT DOCUMENTS 4,160,335 A 7/1979 Von Kohorn et al.
4,923,119 A 5/1990 Yamamoto et al.
5,888,930 A 3/1999 Smith et al.
6,481,639 B1 11/2002 Pozzo
7,048,203 B2 * 5/2006 Harada ............... A01M 1/2044 428/905
7,070,172 B2 * 7/2006 Fabrega .............. A01M 1/2033 261/104
2012/0267279 A1 * 10/2012 Lesniak .................... A61L 9/12 206/524.1
2013/0104445 A1 5/2013 Schneidmiller et al.
2015/0216182 A1 8/2015 Brown et al.
2017/0183426 A1 * 6/2017 Kawai ................... B32B 27/304
2018/0279607 A1 10/2018 Guerret et al.
2020/0038539 A1 * 2/2020 Hu ....................... A01M 1/2044
2020/0222572 A1 * 7/2020 Bourne ................... A61L 9/127
2021/0030913 A1 2/2021 Coals et al.

FOREIGN PATENT DOCUMENTS

GB 2572774 * 10/2019
WO 2021255274 A1 12/2021

OTHER PUBLICATIONS

Air Wick Essentials; https://m.media-amazon.com/images/I/810mldRRe5L.pdf. Published Oct. 10, 2022 (Year: 2022).*
May 15, 2024—International Search Report and Written Opinion, PCT/US2024/014247.

* cited by examiner

*Primary Examiner* — Mina Haghighatian
(74) *Attorney, Agent, or Firm* — POLSINELLI PC

(57) ABSTRACT

The present disclosure provides for non-electrical diffuser devices for use in the treatment of pets or other animals, the device comprising a container for holding a formulation, an outlet, and a passive diffusing element mounted across the outlet for controlling discharge of the formulation from the container.

24 Claims, 3 Drawing Sheets

8
7
9
1
2
4
3
5

5
12
11
10

22
23
5
21
20

32
2
30
36

34
37
30
8
7
9
2
32
34
34
33
4
5
31
36
37

40
47
43
44
46

42
45
ETERNA 46
47
42
40

DIFFUSER DEVICE

INTRODUCTION

This invention relates to diffuser devices for treatment of pets or other animals. In particular, the invention relates to non-electrical diffuser devices for pet behavioural/calming pheromones.

BACKGROUND OF THE INVENTION

Pet behavioural/calming pheromones are available today in a variety of delivery systems, collars, snacks, toys, sprays and mainly heated plug-ins which treat a large area such as a room. The reason for these applications and especially for heated plug-ins is because the current pheromones and not highly volatile. A number of plug-in diffusers are currently available for evaporation of a formulation into a space such as a room to have a calming effect on pets, for example. These usually provide a plug-in device for mounting at a standard electrical socket to power a heater in the device which evaporates the formulation for diffusion throughout the room over a prolonged period. Various stand-alone diffuser devices for mounting on furniture, such as a cabinet or table or on a mantlepiece or window ledge for example, are available and include a battery, or rechargeable battery or can be plugged in to a power supply to operate the heater to diffuse the formulation. A disadvantage of these devices is their limitation to a specific space/room. Also, they require a power supply to diffuse the formulation.

The present invention is directed towards providing an improved diffuser device not requiring a power supply for the release of calming/behavioural pheromones.

SUMMARY OF THE INVENTION

According to the invention there is provided a diffuser device, comprising:

a container for reception of a formulation;

the container having an outlet; and a passive diffusing element mounted across the outlet, the diffusing element being operable to control discharge of the formulation from the container.

In one embodiment of the invention the diffusing element comprises a membrane mounted across the outlet, the membrane being permeable to at least portion of the formulation in vapour form control discharge of said portion of the formulation.

In another embodiment the diffusing element is a wick. In this case the container may conveniently comprise a glass or plastics bottle of any desired size, typically up to about 500 ml, the wick extending within the bottle from the outlet to a bottom of the bottle. The wick may conveniently comprise polyethylene or a polyethylene terephthalate material or any other suitable material.

Advantageously the formulation is sufficiently volatile to passively diffuse in ambient temperature (typically about 10° C. to 40° C.) and does not require a heater for diffusion, thus saving on manufacturing cost and running cost, and affords greater flexibility in positioning/locating the diffuser device for use. The membrane provides for a controlled diffusion of the formulation over a prolonged period, typically up to 30 days and possibly more, and can be controlled through size of the membrane surface and type of membrane or volume or type of formulation.

In another embodiment the pheromone is highly volatile at room temperature.

In another embodiment the vapour pressure of the pheromone is in the range 16.5 to 25 mmHg at 25° C. and preferably is about 17.105 mmHg at 25° C.

In another embodiment the formulation comprises at least one pheromone. It is envisaged that the pheromone will comprise 0.001-5% by weight of this formulation.

In another embodiment the pheromone is for relief of a medical condition such as stress, motion sickness, diet control and the like. That is, for example, the pheromone provides a calming effect on pets.

In another embodiment the pheromone is the rabbit pheromone-trans-2-methyl-2-butenal.

In another embodiment the formulation can include a fragrance and/or a colour.

In another embodiment, the formulation includes a solvent.

In another embodiment, the formulation can be a microemulsion.

In another embodiment, the formulation includes paraffin wax.

In another embodiment the formulation is provided in a liquid or gel form.

In another embodiment, the formulation includes a gelling agent.

In one embodiment of the invention the container, tray or holder is vacuum-formed from a multi-layer plastics sheet.

In another embodiment the container, tray or holder has a first layer comprising PET (polyethylene terephthalate), a second layer comprising polyethylene and a third layer comprising copolymer EVOH (ethylene-vinyl alcohol copolymer). Other layered plastics films are possible also.

In another embodiment the membrane comprises polyethylene, polypropylene or other material.

In another embodiment a peel-away sealing sheet is mounted across an outer face of the membrane to seal the membrane before use.

In another embodiment the peel-away sealing sheet comprises an aluminium foil and/or plastics material.

In another embodiment, a holder is provided upon which the container is supported or held.

In another embodiment the holder could be a table-top stand to treat a room for example, or a compact unit such as a pendant which can be worn by a pet or other animal. Thus advantageously, a pet wearing the compact unit would always be in the presence of the area of treatment by the pheromone, not just when they are in a specific treated space or room. Alternatively, the diffuser device may be adapted for attachment to veterinary Elizabethan collars. In this case a base of the container may be at least partially coated with adhesive covered by a peel-away cover sheet.

The holder may be constructed of any suitable material, including metal, plastics, wood and cardboard.

In another embodiment, the container may be a plastic or glass container with a wick extending to the bottom of the container.

BRIEF DESCRIPTION OF THE DRAWINGS

The invention will be more clearly understood from the following description of some embodiments thereof, given by way of example only, with reference to the accompanying drawings, in which.

DETAILED DESCRIPTION OF THE PREFERRED EMBODIMENTS

Figures 1, 2, 3:
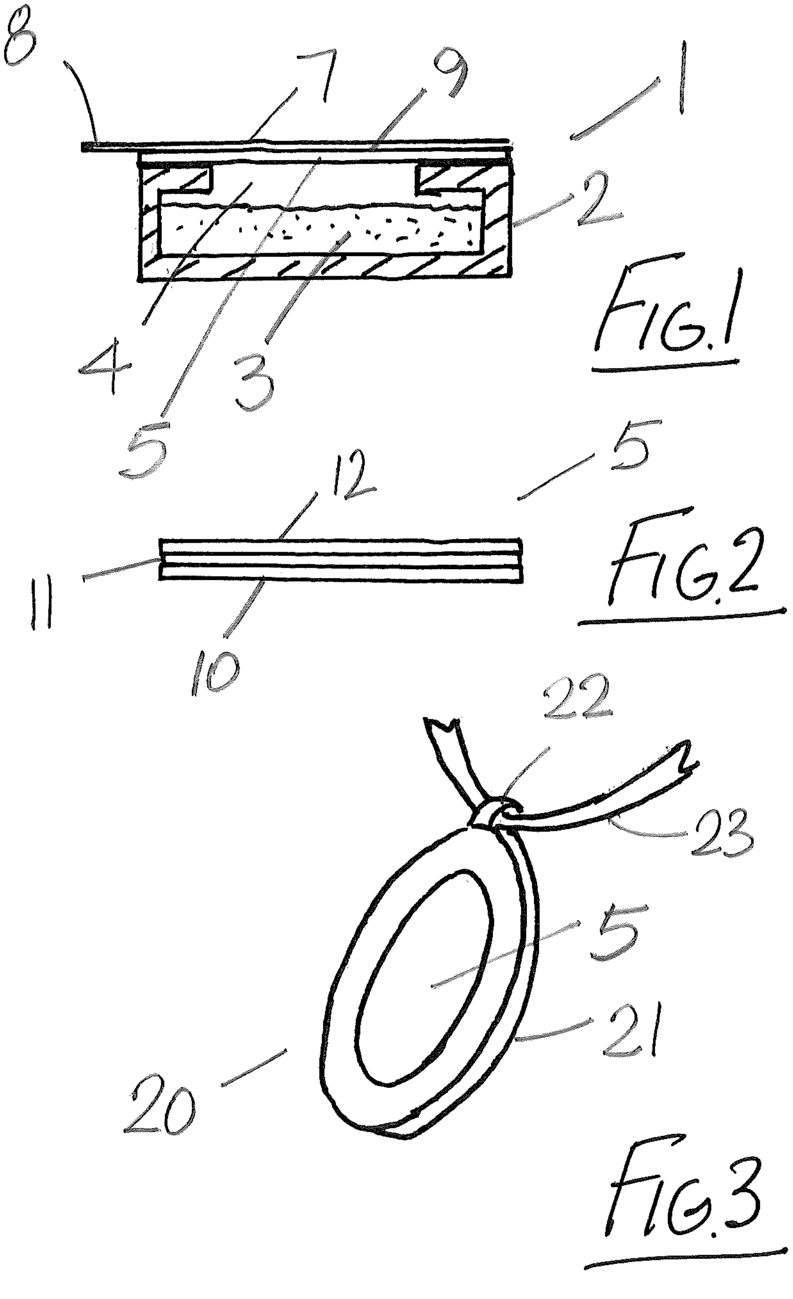
FIG. 1 is a schematic sectional elevational view of a diffuser device according to the invention.
FIG. 2 is a detail elevational view of a diffuser membrane forming portion of the diffuser device.
FIG. 3 is a perspective view of another diffuser device according to a second embodiment of the invention.

Referring to the drawings, and initially to FIG. 1 and FIG. 2 thereof, there is illustrated a diffuser device according to the invention, indicated generally by the reference numeral 1. The diffuser device 1 has a container 2 for reception and storage of a volatile formulation 3 in liquid or gel form and containing a selected pheromone which is sufficiently volatile to passively diffuse at ambient temperature. An outlet 4 of the container 2 is covered by a membrane 5 which is permeable to the volatile formulation 3 when in vapour form to diffuse the vapour through the membrane 5 in a controlled manner over an extended period of time, typically about 30 days or more. The formulation may, for example, be chosen to have a calming or behavioural effect on pets. Different formulations to achieve different effects are possible. A peel-away aluminium foil sealing sheet 7 with pull tab 8 covers an external face 9 of the membrane 5.

The pheromone is for relief of a medical condition such as stress, motion sickness, diet control and the like. For example, the pheromone can be chosen to provide a calming effect on pets. The pheromone is highly volatile at room temperature having a vapour pressure in the range 16.5 to 25 mmHg at 25° C. and preferably is about 17.105 mmHg at 25° C. The pheromone comprises 0.001-5% by weight of the formulation. Preferably the pheromone is the rabbit pheromone-trans-2-methyl-2-butenal.

FIG. 2 shows a multi-layer plastics sheet used to form the container 2 having an inner first layer 10 of PET, an intermediate second layer 11 of polyethylene and an outer third layer 12 of copolymer EVOH. The membrane 5 is of polypropylene material.

Referring now to FIG. 3 there is illustrated a diffuser device according to a second embodiment of the invention, indicated generally by the reference numeral 20. Parts similar to those described previously are assigned the same reference numerals. In this case the container 2 is mounted within a holder which in this case is in the form of a pendant 21 having a loop 22 for reception of a tie 23, which could be a cord or chain for example, so that the pendant 21 can be worn about a pet's neck or attached to a pet's collar. Thus, the pet is constantly in the presence of the active pheromone vapour.

Figures 4, 5:
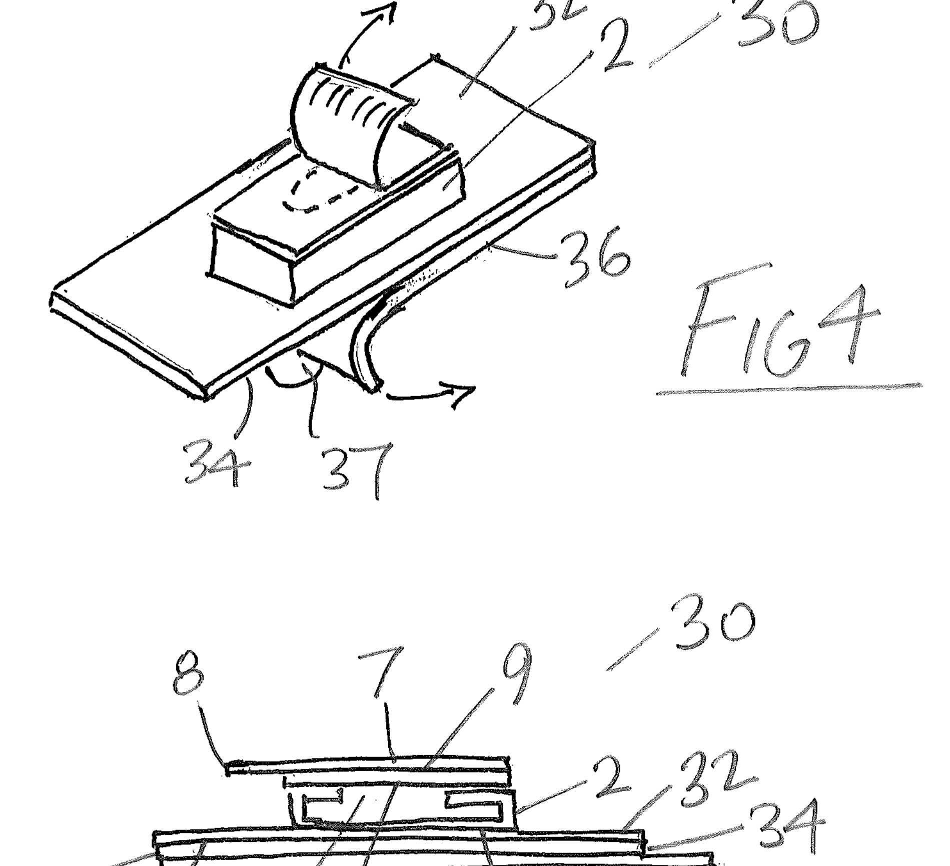
FIG. 4 is a perspective view of a diffuser device according to a third embodiment of the invention.
FIG. 5 is a schematic sectional elevational view of the diffuser device shown in FIG. 4.

Referring now to FIG. 4 and FIG. 5, there is illustrated a diffuser device according to a third embodiment of the invention, indicated generally by the reference numeral 30. Parts similar to those described previously are assigned the same reference numerals. In this case a bottom 31 of the container 2 is attached to a holder formed by a mounting strip 32. An underside 33 of the mounting strip 32 is coated with a layer of adhesive 34. A peel-away cover sheet 36 with outwardly projecting grip tab 37 covers the adhesive layer 34 prior to use. Double-sided adhesive tape could alternatively be used.

After removing the cover sheet 36 the device 30 can be attached to an Elizabethan collar or other pet collar. With the foil sealing sheet 7 removed the gradual diffusion of pheromone from the container 2 maintains a calming atmosphere at the pet wearing the collar. In an alternative arrangement the mounting strip 32 could be attached to a support surface such as a table, a wall or a window in a room or vehicle frequented by the pet.

Figures 6, 7, 8:
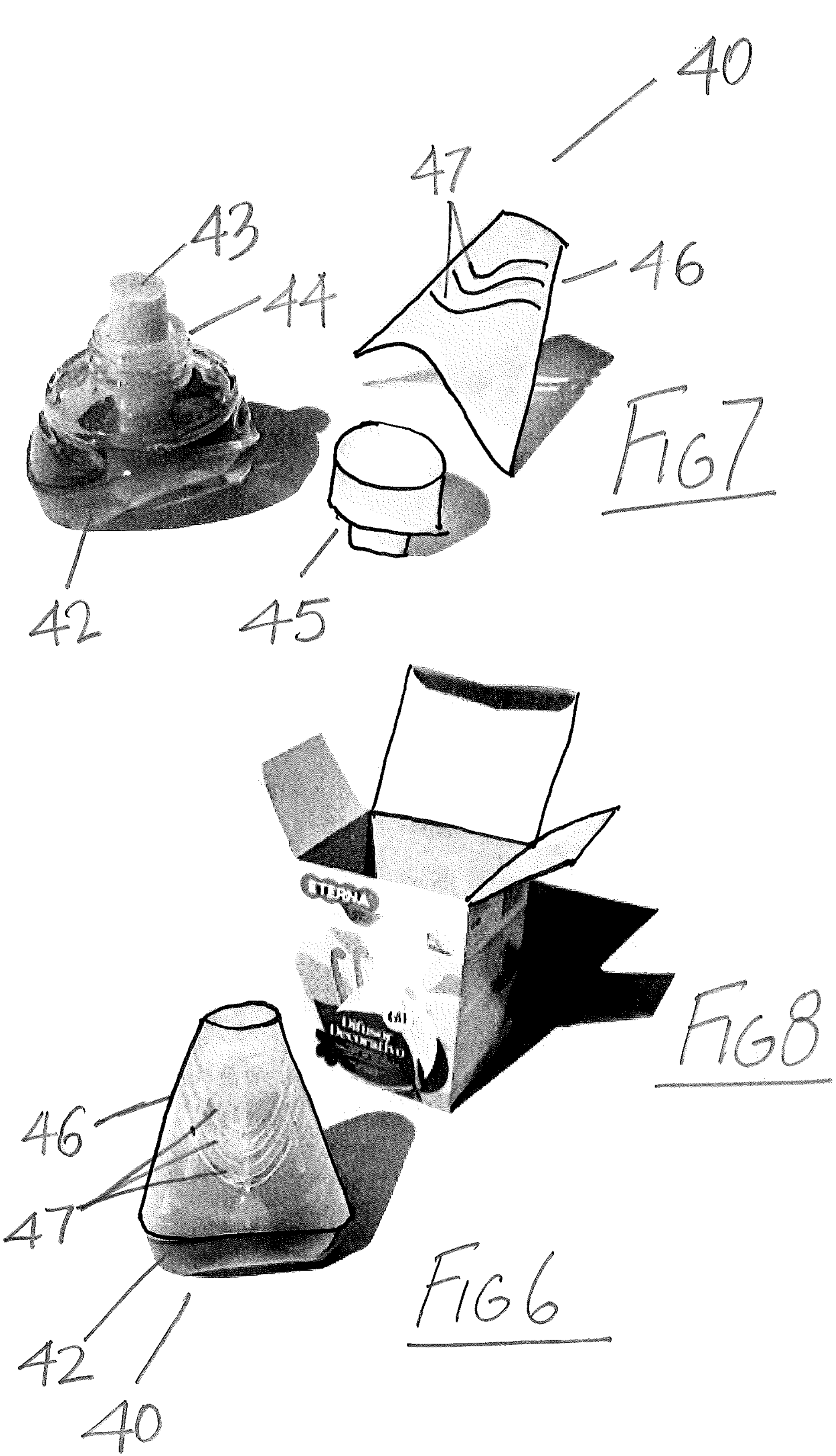
FIG. 6 is a perspective view of a diffuser device according to a fourth embodiment the invention.
FIG. 7 is an exploded perspective view of the diffuser device shown in FIG. 6.
FIG. 8 is a perspective view of a packaging carton for the diffuser device of FIG. 6.

Referring now to FIG. 6 to FIG. 8, there is illustrated a diffuser device according to a fourth embodiment of the invention, indicated generally by the reference numeral 40. Parts similar to those described previously are assigned the same reference numerals. In this case the container comprises a plastics or glass bottle 42 which contains the formulation. A wick 43 forming the diffusing element is mounted in the neck 44 outlet of the bottle 42 and extends within the bottle 42 to the bottom of the bottle 42. A cap 45 engages with the neck 44 to seal the bottle 42 prior to use or when not in use. Upon removal of the cap 45 a decorative diffuser cowl 46 with vent openings 47 engages and sits on the bottle 42 housing the wick 43 within the cowl 46. The formulation is gradually dispensed from the bottle through the wick 43. Diffusion of the formulation can be stopped by replacing the cap 45 on the bottle 42.

The size of the container used can be chosen depending on the volume of formulation required, the desired length of treatment and the area to be treated.

In this specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in both construction and detail within the scope of the appended claims.

The invention claimed is:

1. A compact diffuser device, comprising:

(a) a container having solid walls enclosing a space defining a chamber for reception of a formulation, the container having an outlet and comprising:
  i. a first layer comprising polyethylene terephthalate (PET);
  ii. a second layer comprising polyethylene; and
  iii. a third layer comprising ethylene-vinyl alcohol copolymer (EVOH copolymer);

(b) a passive diffusing element covering the outlet and operable to control discharge of the formulation from the container, wherein the diffusing element is an intact membrane mounted across the outlet, the membrane being permeable to at least portion of the formulation in vapour form to control discharge of the portion of the formulation for about 30 days;

(c) a formulation contained within the container, the formulation being sufficiently volatile to passively diffuse at ambient temperature and comprising a pheromone having a vapour pressure of from about 16.5 mmHg to about 25 mmHg and wherein the formulation is in the chamber at a level below the outlet and the intact membrane; and (d) a solid holder comprising an upper surface and a bottom surface, wherein the bottom of the container is attached to the upper surface of the holder, the container positioned within the upper surface of the holder, and the bottom surface of the holder comprising a mounting strip, and wherein the underside of mounting strip comprises a peel-away cover sheet with outwardly projecting grip tab;

wherein the diffuser is a non-electrical diffuser, and is sufficiently compact for use on an animal.

2. The diffuser device of claim 1, wherein the pheromone is highly volatile at room temperature.

3. The diffuser device of claim 2, wherein the vapour pressure of the pheromone is about 17.105 mmHg at 25° C.

4. The diffuser device of claim 2, wherein the formulation comprises the pheromone at 0.001-5% by weight of the formulation.

5. The diffuser device of claim 2, wherein the pheromone provides relief of a condition selected from stress, motion sickness, and diet control.

6. The diffuser device of claim 5, wherein the pheromone provides a calming effect on pets.

7. The diffuser device of claim 2, wherein the pheromone is trans-2-methyl-2-butenal.

8. The diffuser device of claim 1, wherein the formulation further comprises a fragrance or a colour.

9. The diffuser device of claim 1, wherein the formulation further comprises a solvent.

10. The diffuser device of claim 1, wherein the formulation further comprises a paraffin wax.

11. The diffuser device of claim 1, wherein the formulation is a micro-emulsion.

12. The diffuser device of claim 1, wherein the formulation is a liquid or a gel.

13. The diffuser device of claim 1, wherein the formulation comprises a gelling agent.

14. The diffuser device of claim 1, wherein the container is vacuum-formed from a multi-layer plastics sheet.

15. The diffuser device of claim 1, wherein the membrane comprises a material selected from polyethylene or polypropylene.

16. The diffuser device of claim 15, further comprising a peel-away sealing sheet mounted across an outer face of the membrane.

17. The diffuser device of claim 16, wherein the peel-away sealing sheet comprises a material selected from an aluminium foil and a plastic.

18. The diffuser device of claim 1, further comprising a holder upon which the container is supported.

19. The diffuser device of claim 18, wherein the holder is a table-top stand.

20. The diffuser device of claim 18, wherein the holder is a compact unit configured to be worn by a pet.

21. The diffuser device of claim 1, wherein the diffuser device is adapted for attachment to veterinary Elizabethan collars (E-collars), a base of the container being at least partially coated with adhesive covered by a peel-away cover sheet.

22. The diffuser device of claim 20, wherein the compact unit is a pendant.

23. A non-electrical diffuser device, comprising:

(a) a solid container forming a single body comprising a plastic or glass bottle having walls enclosing a space for reception of a formulation which is sufficiently volatile to passively diffuse at ambient temperature, the body having a neck forming an outlet, wherein the neck has a smaller diameter relative to the diameter of the body;

(b) a cap configured to engage with the neck to seal the bottle prior to use or when not in use;

(c) a wick comprising polyethylene or polyethylene terephthalate mounted at the neck of the container at the outlet and extending within the container from the outlet to a bottom of the container;

(d) a cowl with one or more vent openings on the side, the cowl being configured to engage with and be postitionable on the container housing the wick after removal of the cap;

(e) a formulation contained within the container, the formulation comprising a pheromone having a vapour pressure of from about 16.5 mmHg to about 25 mmHg.

24. A non-electrical diffuser device, comprising:

(a) a container having solid walls enclosing a space for reception of a formulation which is sufficiently volatile to passively diffuse at ambient temperature, the container having an outlet (b) a passive diffusing element mounted across and covering the outlet and operable to control discharge of the formulation from the container, wherein the diffusing element is an intact membrane comprising polyethylene or polypropylene which is permeable to at least portion of the formulation in vapour form;

(c) a solid holder supporting the container, wherein the holder:

i. is configured as a pendant comprising a loop for reception of a tie, cord, or a chain operable to be worn around a pet's neck; or ii. comprises a mounting strip comprising an adhesive layer covered by a peel away cover sheet operable to be attached to an Elizabethan collar or a pet collar; and (d) a formulation contained within the container, the formulation comprising a pheromone having a vapour pressure of from about 16.5 mmHg to about 25 mmHg.

* * * * *